(12) United States Patent
Li et al.

(10) Patent No.: US 11,331,345 B2
(45) Date of Patent: May 17, 2022

(54) PD-1 CAR NK-92 CELL AND PREPARATION METHOD AND USE THEREOF

(71) Applicant: Asclepius (Suzhou) Technology Company Group Co., Ltd., Suzhou (CN)

(72) Inventors: Huashun Li, Suzhou (CN); Baolei Wang, Suzhou (CN); Kunkun Han, Suzhou (CN); Baoyong Ren, Suzhou (CN)

(73) Assignee: ASCLEPIUS (SUZHOU) TECHNOLOGY COMPANY GROUP CO., LTD., Suzhou (CN)

( * ) Notice: Subject to any disclaimer, the term of this patent is extended or adjusted under 35 U.S.C. 154(b) by 469 days.

(21) Appl. No.: 16/389,954

(22) Filed: Apr. 21, 2019

(65) Prior Publication Data
US 2019/0240258 A1 Aug. 8, 2019

Related U.S. Application Data

(63) Continuation of application No. PCT/CN2016/104493, filed on Nov. 4, 2016.

(30) Foreign Application Priority Data

Oct. 26, 2016 (CN) .......................... 201610944672.7

(51) Int. Cl.
| | |
|---|---|
| *A61K 35/17* | (2015.01) |
| *C07K 14/47* | (2006.01) |
| *A61P 35/00* | (2006.01) |
| *C12N 15/86* | (2006.01) |
| *A61K 48/00* | (2006.01) |
| *C12N 15/62* | (2006.01) |
| *C12N 15/867* | (2006.01) |
| *C12N 5/10* | (2006.01) |
| *C07K 19/00* | (2006.01) |

(52) U.S. Cl.
CPC .............. *A61K 35/17* (2013.01); *A61K 48/00* (2013.01); *A61P 35/00* (2018.01); *C07K 14/4702* (2013.01); *C07K 19/00* (2013.01); *C12N 5/10* (2013.01); *C12N 15/62* (2013.01); *C12N 15/86* (2013.01); *C12N 15/867* (2013.01)

(58) Field of Classification Search
CPC ...................................................... A61K 35/17
See application file for complete search history.

(56) References Cited

FOREIGN PATENT DOCUMENTS

| | | | |
|---|---|---|---|
| CN | 104114233 A | 10/2014 | |
| CN | 105132445 A | 12/2015 | |
| CN | 105246504 A | 1/2016 | |
| CN | 105392888 A | 3/2016 | |
| CN | 105907719 A | 8/2016 | |
| WO | 2015090229 A1 | 6/2015 | |
| WO | 2015142675 A2 | 9/2015 | |
| WO | WO2015/142675 * | 9/2015 | ............. A61K 39/00 |
| WO | 2015193411 A1 | 12/2015 | |

OTHER PUBLICATIONS

First Office Action for Application No. or Publication No. 2016109446727, The State Intellectual Property Office of People's Republic of China.
Patent Cooperation Treaty, Written Opinion of the International Searching Authority, International Application No. PCT/CN2016/104493.
International Search Report for International Application No. PCT/CN2016/104493, Nucleotide and/or amino acid sequence(s).
NIH Public Access Author Manuscript, Sep. 2013, NK cell biology: An update and future directions, J allergy Clin Immunol.
Chin J Cancer Biother., Apr. 2016, vol. 23, No. 2, The current situation and prospect of immunocyte-therapy for tumor, Guo Zhenhong.

* cited by examiner

*Primary Examiner* — Scott Long
(74) *Attorney, Agent, or Firm* — Flener IP & Business Law; Zareefa B. Flener

(57) ABSTRACT

Provided are a PD-1 CAR NK-92 cell and a preparation method and use thereof. The PD-1 CAR NK-92 cell expresses PD-1-CD8™-4-1BB-CD3ζ fusion protein in NK-92 cells. The PD-1 CAR NK-92 is obtained by infecting an NK92 cell line with a PD-1 CAR molecule and obtaining monoclonal cells by means of flow screening, and culturing and expanding CAR NK92 monoclonal cell strains with stable traits and a high killing activity. The cells can be produced on a large scale, can be used in different patients without GVHR rejection, and have a specific killing activity and significant therapeutic effect on tumors.

19 Claims, 3 Drawing Sheets

Specification includes a Sequence Listing.

PD-1 CAR NK-92 CELL AND PREPARATION METHOD AND USE THEREOF

CROSS-REFERENCE TO RELATED APPLICATION

This application is a continuation application of International patent application No. PCT/CN2016/104493, filed on Nov. 4, 2016, which claims the benefit and priority of Chinese patent application No. CN201610944672.7, filed on Oct. 26, 2016, each of which is incorporated herein by reference in its entirety and for all purposes.

FIELD OF THE INVENTION

The present invention relates to a cell and a preparation method and use thereof, in particular to a PD-1 CAR NK-92 cell and a preparation method and use thereof.

BACKGROUND OF THE INVENTION

With the gradual development of tumor immunotherapy research, programmed death growth factor-1 (PD-1/CD 279) and its ligands PD-L1/2 (B7-H1/CD274) have been favored by many researchers as important members in tumor microenvironment. On Sep. 4, 2014, the U.S. Food and Drug Administration (FDA) approved Keytruda (pembrolizumab) for use in patients with advanced or unresectable melanoma who have failed to respond to other medications, and Keytruda became the first FDA-approved drug to block the PD-1 cell pathway. PD-1 was first discovered in 1992, mainly expressed in T cells, regulatory T cells, "exhausted" T cells, B cells, activated monocytes, dendritic cells, natural killer cells, and natural killer T cells, etc. PD-1 is generally expressed in activated T cells, which comprises a transmembrane domain, a stem domain, an Ig superfamily domain and an intracellular domain containing ITIM and ITSM. PD-1 is a synergistic inhibitory receptor, and has two ligands, PD-L1 and PD-L2. PD-L 1 is abnormally expressed in different malignant tumors, such as lung, esophageal, head and neck squamous cell carcinomas, and in other types of malignancies, such as ovarian cancer, bladder cancer, malignant melanoma and glioma. Structurally, PD-L2 is similar to PD-L1, both being type I transmembrane proteins comprised of a signal peptide, an IgV-like domain, an IgC-like domain, a stem domain, a transmembrane domain, and a cytoplasmic domain. Binding of PD-1 to the ligand PD-L1/PD-L2 results in the phosphorylation of tyrosine in ITIM and ITSM, and promotes the binding of SH P-1 and SH P-2 to ITIM and ITSM bind, which in turn delivers T cell inhibitory signals and indirectly leads to cell death through the down-regulated expression of BC L•X L and the differentiation of T cells. PD-1 PD-L 1/2 pathway is also considered to be a pathway mediating immunosuppression, with PD-1 working as a negative regulatory checkpoint. The inhibitory function of PD-1 and PD-L1 pathways can enhance T cell responses in vitro; and in vivo, PD-1 binds to the specific ligands (PD-L1, PD-L2) to down-regulate antigen-stimulated lymphocyte proliferation and cytokine production, ultimately leading to lymphocyte "deleption" and inducing immune tolerance. Tumor cells in solid tumors may up-regulate the expression of PD-L1, which in turn provides an inhibitory signal for down-regulating activated T cells, ultimately turning off immune response and inducing immune tolerance. The survival rate of patients with high expression level of PD-L1 significantly decreases, which is consistent with the most reports describing the association of the high expression level of PD-L1 on tumor cells with poor prognosis. In addition to expression in malignant melanoma, PD-L1 may also be expressed in other different tumors, including glioblastoma, pancreatic cancer, ovarian cancer, breast cancer, renal cell carcinoma, head and neck and esophageal squamous cell carcinoma, and non-small cell lung cancer, moreover, high expression of PD-L1 on tumor cells is associated with poor prognosis.

Natural killer (NK) cells are important effector cell types for cancer adoptive immunotherapy. Similar to T cells, NK cells may be modified to express chimeric antigen receptors (CARs) to enhance anti-tumor activity. The successful application of CD19 CAR-T cells in patients with CD19-positive malignancies proved the feasibility of this method for cancer immunotherapy (see e.g. Grupp et al., 2013). CAR-T cells target a variety of different tumor antigens and are being actively developed for clinical development (Kalos et al., 2013). There are few CAR NK cell immunotherapy attempts for natural killer (NK) cells, and so far no clinical data is available for this practice. NK cells play an important role in cancer immune surveillance and represent important effector cell types for cancer adoptive immunotherapy. Compared to T cells, they do not require prior activation and recognition of peptide antigens presented by complex MHC molecules. In contrast, NK cells can exhibit killing activity under appropriate stimulation by coupling the CD3ζ molecule to the encoded cell surface receptor. Thus, NK cells containing the CD3ζ-CAR element are readily linked to endogenous signaling pathways and trigger cytolytic activity. Despite these advances, experience in clinical development of CAR NK cells remains limited.

Phase I studies have shown that unmodified NK-92 cells, which have been irradiated prior to application, have demonstrated safety in clinical applications. However, it did not show significant anti-tumor activity, probably due to the lack of tumor-specific receptors in unmodified NK-92 cells, and the inability to recognize tumors.

The present inventors preliminarily prepared PD-1 CAR-T cells to treat tumors, however, the PD-1 CAR-T cells have the following disadvantages that: CAR-T cells have a graft versus host reaction (GVHR) between different individuals; they need to be individually customized and can only be used in a single patient, and resulting in taking a long time; their preparation is inclined to failure when the patient's T cell is in poor condition; and CAR-T prepared by different patient-derived T cells has inconsistent activity, which leads to unstable drug effects, etc. The above problems need to be solved urgently.

SUMMARY OF THE INVENTION

The present invention provides a PD-1 CAR NK-92 cell and a preparation method and use thereof, to solve the problem that the CAR-T prepared by different patient-derived T cells has unstable drug effect caused by inconsistent activity.

In order to achieve the above object, the present invention is achieved by the following technical solutions:

The present invention provides a PD-1 CAR NK-92 cell, which may express a PD-1-CD8™-4-1BB-CD3ζ fusion protein in a NK-92 cell, the NK-92 cell is derived from ATCC® CRL2407™, and the extracellular portion of the PD-1 protein in the PD-1-CD8™-4-1BB-CD3ζ fusion protein has:

a) an amino acid sequence as shown in SEQ ID NO: 5, or b) an amino acid sequence derived from a) by substituting and/or deleting and/or adding one or several amino acid residues and having the same function.

The CD8™ in the PD-1-CD8™-4-1BB-CD3ζ fusion protein has: an amino acid sequence as shown in SEQ ID NO: 1; or, an amino acid sequence derived from the amino acid sequence as shown in SEQ ID NO: 1 by substituting and/or deleting and/or adding one or several amino acid residues and having the same function.

The 4-1BB in the PD-1-CD8™-4-1BB-CD3ζ fusion protein has: an amino acid sequence as shown in SEQ ID NO: 2; or, an amino acid sequence derived from the amino acid sequence as shown in SEQ ID NO: 2 by substituting and/or deleting and/or adding one or several amino acid residues and having the same function.

The 4-1BB in the PD-1-CD8™-4-1BB-CD3ζ fusion protein may be replaced by CD28, and the CD28 has a molecular sequence as shown in SEQ ID NO: 3; or, an amino acid sequence derived from the amino acid sequence as shown in SEQ ID NO: 3 by substituting and/or deleting and/or adding one or several amino acid residues and having the same function.

The CD3ζ in the PD-1-CD8™-4-1BB-CD3ζ fusion protein has: an amino acid sequence as shown in SEQ ID NO: 4; or, an amino acid sequence derived from the amino acid sequence as shown in SEQ ID NO: 4 by substituting and/or deleting and/or adding one or several amino acid residues and having the same function.

The PD-1-CD8™-4-1BB-CD3ζ fusion protein has: an amino acid sequence as shown in SEQ ID NO: 6; or, an amino acid sequence derived from the amino acid sequence as shown in SEQ ID NO: 6 by substituting and/or deleting and/or adding one or several amino acid residues and having the same function.

The present invention also provides a gene encoding a fusion protein PD-1-CD8™-4-1BB-CD3. The gene of the fusion protein PD-1-CD8™-4-1BB-CD3ζ has a sequence as shown in SEQ ID NO: 7; or, a DNA molecule hybridizing with the sequence as shown in SEQ ID NO: 7 under stringent conditions and encoding a related protein having a function of preventing and/or treating a tumor; or, a DNA molecule having at least 90% or more, or 95% or more, or 98% or more homology to the sequence as shown in SEQ ID NO: 7 and encoding a related protein having a function of preventing and/or treating a tumor.

The gene of PD-1 in the fusion protein PD-1-CD8™-4-1BB-CD3ζ has a sequence as shown in SEQ ID NO: 8; or, a DNA molecule hybridizing with the sequence as shown in SEQ ID NO: 8 under stringent conditions and encoding a related protein having a corresponding function; or, a DNA molecule having at least 90% or more, or 95% or more, or 98% or 98% or more homology to the sequence as shown in SEQ ID NO: 8 and encoding a related protein having a corresponding function.

The gene of CD 8 Hinge in the fusion protein PD-1-CD8™-4-1BB-CD3ζ has a sequence as shown in SEQ ID NO: 9; or, a DNA molecule hybridizing with the sequence as shown in SEQ ID NO: 9 under stringent conditions and encoding a related protein having a corresponding function; or, a DNA molecule having at least 90% or more, or 95% or more, or 98% or 98% or more homology to the sequence as shown in SEQ ID NO: 9 and encoding a related protein having a corresponding function.

The gene of CD8™ in the fusion protein PD-1-CD8™-4-1BB-CD3ζ has a sequence as shown in SEQ ID NO: 10; or, a DNA molecule hybridizing with the sequence as shown in SEQ ID NO: 10 under stringent conditions and encoding a related protein having a corresponding function; or, a DNA molecule having at least 90% or more, or 95% or more, or 98% or 98% or more homology to the sequence as shown in SEQ ID NO: 10 and encoding a related protein having a corresponding function.

The gene of 4-1BB in the fusion protein PD-1-CD8™-4-1BB-CD3ζ has a sequence as shown in SEQ ID NO: 11; or, a DNA molecule hybridizing with the sequence as shown in SEQ ID NO: 11 under stringent conditions and encoding a related protein having a corresponding function; or, a DNA molecule having at least 90% or more, or 95% or more, or 98% or 98% or more homology to the sequence as shown in SEQ ID NO: 11 and encoding a related protein having a corresponding function.

The gene of CD3ζ in the fusion protein PD-1-CD8™-4-1BB-CD3ζ has a sequence as shown in SEQ ID NO: 12; or, a DNA molecule hybridizing with the sequence as shown in SEQ ID NO: 12 under stringent conditions and encoding a related protein having a corresponding function; or, a DNA molecule having at least 90% or more, or 95% or more, or 98% or 98% or more homology to the sequence as shown in SEQ ID NO: 12 and encoding a related protein having a corresponding function.

The present invention also provides a biological material related to a fusion protein PD-1-CD8™-4-1BB-CD3ζ containing the gene encoding the fusion protein PD-1-CD8™-4-1BB-CD3ζ of the present invention, which includes a recombinant vector, an expression cassette, a recombinant cell, a recombinant bacterium and a recombinant virus. Preferably, the recombinant vector of the present invention is a recombinant expression vector or a recombinant cloning vector.

The fusion protein of the present invention may be artificially synthesized, or may also be obtained by first synthesizing the coding gene thereof followed by biological expression.

The present invention also provides a preparation method of a PD-1 CAR NK-92 cell, including the steps of:

(1) synthesizing and amplifying a gene of the PD-1-CD8™-4-1BB-CD3ζ fusion protein, and cloning the gene of PD-1-CD8™-4-1BB-CD3ζ fusion protein into a lentiviral expression vector;

(2) infecting a 293T cell with a lentiviral packaging plasmid and the lentiviral expression vector plasmid obtained in the step (1), packaging and preparing a lentivirus;

(3) staining a NK-92 cell with PD1 antibody, sorting PD1-CAR NK-92 positive cells and expanding to obtain the PD-1 CAR NK-92 cells.

In the step (3), the density of the NK-92 cells is adjusted to $2\text{-}3\times10^5$/ml.

The present invention further provides a pharmaceutical composition comprising PD-1 CAR NK-92 cells prepared from PD-1-CD8™-4-1BB-CD3ζ fusion protein, and a pharmaceutically acceptable adjuvant.

The pharmaceutical composition of the present invention may be a tablet (including a sugar-coated tablet, a film-coated tablet, a sublingual tablet, an orally disintegrating tablet, an oral tablet, etc.), a pill, a powder, a granule, a capsule (including a soft capsule, a microcapsule), a lozenge, a syrup, a liquid, an emulsion, a suspension, a controlled release preparation (for example, a transient release preparation, a sustained release preparation, a sustained release microcapsule), an aerosol, a film (for example, an orally disintegrating film, an oral mucosa-adhesive film), an injection (for example, an subcutaneous injection, an intravenous injection, an intramuscular injection, an intraperitoneal injection), an intravenous drip, a transdermal absorption preparation, an ointment, a lotion, an adhesive preparation, a suppository (for example, a rectal suppository, a vaginal suppository), a small pill, a nasal preparation, a pulmonary preparation (an inhalation), an eye drop, etc., an oral or parenteral preparation (for example, through intravenous, intramuscular, subcutaneous, intra-organ, intranasal, intradermal, instillation, intracerebral, intrarectal and other dosage forms, the drug is given to the vicinity of a tumor and directly given to the lesion). Preferably, the pharmaceutical composition is an injection.

The pharmaceutically acceptable adjuvant of the present invention is preferably a pharmaceutically acceptable adjuvant for injection, such as isotonic sterile saline solution (sodium dihydrogen phosphate, disodium hydrogen phosphate, sodium chloride, potassium chloride, calcium chloride, magnesium chloride, etc., or a mixture of the above salts). Or, for a dried, for example, freeze-dried composition, sterile water or physiological saline may be suitably added thereto to form an injectable solute.

The present invention also provides the use of PD-1 CAR NK-92 cells prepared from PD-1-CD8™-4-1BB-CD3ζ fusion protein in the preparation of medicaments for preventing and/or treating tumors; preferably, the use of the PD-1 CAR NK-92 cells in the preparation of medicaments for preventing and/or treating tumors which highly expresses PDL-1 molecules.

In the present invention, the term "prevention", "preventing" or "treatment", "treating" includes therapeutic or prophylactic treatment or measures with the goal of preventing or slowing down a targeted pathological condition or disorder. A subject is successfully "prevented" or "treated" if receiving a therapeutic amount of the fusion protein of the present invention according to the method of the present invention, the subject shows an observable and/or measurable reduction or disappearance of one or more signs and symptoms of a particular disease.

An advantage and a beneficial effect of the present invention resides in that: the present invention provides a PD-1 CAR NK-92 cell, which does not need to isolate a patient's peripheral blood mononuclear cells (PBMC) compared to CAR-T cells, and does not require specific activation of T cells and preparation of CAR-T cells (this process requires the patient to wait more than 10 days), does not require individual customization, and can be used for multiple patients, shortening the time, and the PD-1 CAR-NK92 cells can be prepared in large quantities and used immediately by patients; on the other hand, the conventionally prepared CAR-T cells are obtained by virus infection of T cells isolated from patients, wherein the T cells are not the same monoclonal source, while the sorted CAR-NK92 cells are derived from the same single clone, which are uniform and stable in characters and activity, and facilitate large-scale production and quality control. Furthermore, compared with NK92 cells, the CAR-NK92 cells have a specific killing activity and significant therapeutic effect on tumors due to the introduction of the PD-1 CAR vector.

The PD-1 CAR NK-92 of the present invention is obtained by infecting PD-1 CAR molecules into NK92 cell line and screening to obtain a single cloned cell by flow cytometry, and culturing and expanding the CAR NK92 monoclonal cell strain with stable traits and high killing activity. The cells can be produced on a large scale and can be used in different patients without GVHR rejection.

BRIEF DESCRIPTION OF THE DRAWINGS

In order to more clearly illustrate the embodiments of the present invention or the technical solutions in the prior art, the drawings used in the embodiments or the description of the prior art will be briefly described below. Obviously, the drawings in the following description are only some of the embodiments of the present invention, and those skilled in the art can obtain other drawings according to these drawings without any inventive labor.

DETAILED DESCRIPTION OF THE INVENTION

The specific embodiments of the present invention are further described below in conjunction with the drawings and examples. The following examples are only intended to more clearly illustrate the technical solutions of the present invention, and are not intended to limit the scope of the present invention.

EXAMPLE 1

Preparation of a Lentiviral Expression Vector

Figure 1:
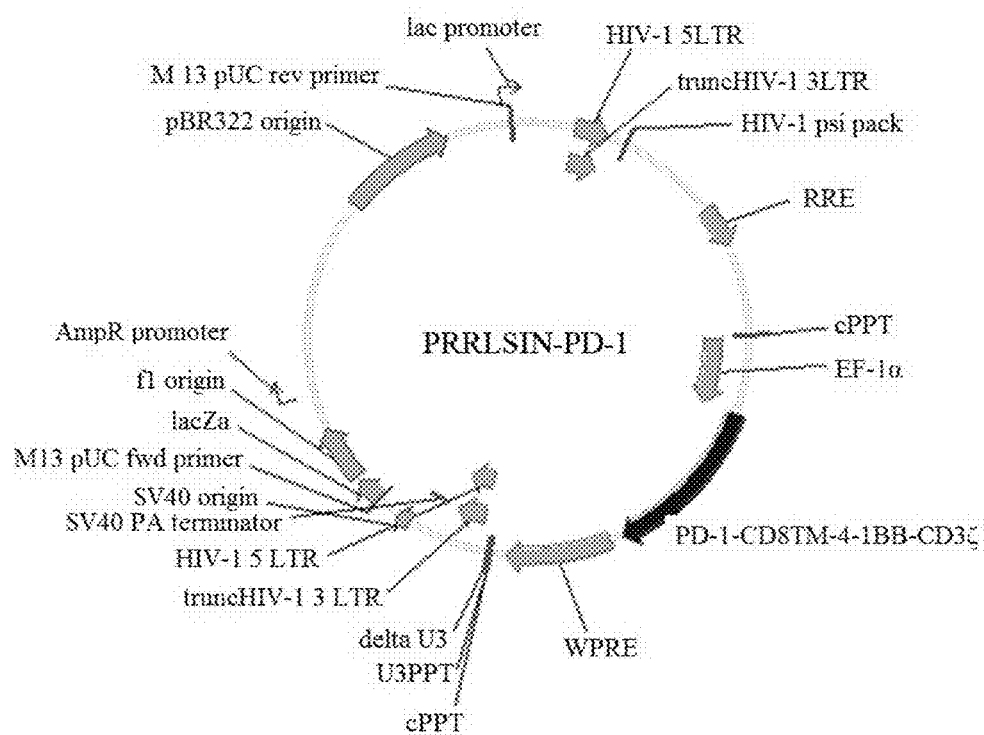
FIG. 1 is a graph of the lentiviral plasmid vector PRRLSIN-PD-1.
Figure 2:
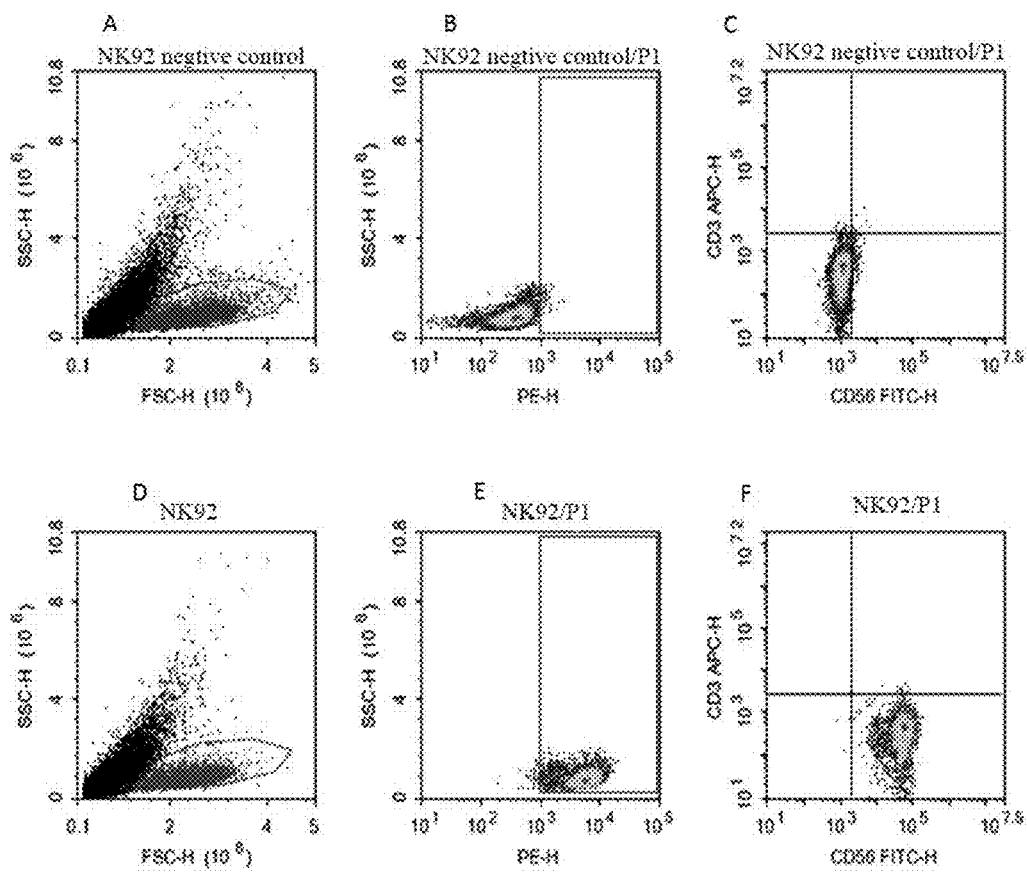
FIG. 2 is a flow cytometry map of PD-1 CAR NK-92.

The PD-1-CD8™-4-1BB-CD3ζ fusion gene sequence was synthesized and ligated into a PRRSLIN vector by enzymatic digestion and transformation, wherein the upstream of the gene was an EF-1α promoter. The vector was transformed into Stbl3 *Escherichia coli* strain. Positive clones were obtained by screening with ampicillin Plasmids were extracted. Clones were identified by enzymatic digestion, and pRRSLIN-PD-1 lentiviral transfection vector was obtained. The vector construction map is shown in FIG. 1.

EXAMPLE 2

Preparation of Lentivirus (1) 24 hours prior to transfection, 293T cells were inoculated into a 15 cm culture dish at a cell density of approximately $8 \times 10^6$ per dish. It was ensured that the cells were at a confluence of about 80% and evenly distributed in the culture dish at the time of transfection.

(2) Preparation of Solution A and Solution B

Solution A: 6.25 mL 2×HEPES buffer (the amount of 5 large dishes packaged together worked best).

Solution B: A mixture with the following plasmids separately added: 112.5 μg pRRSLIN-PD-1 (target plasmid); 39.5 μg pMD2.G (VSV-G envelop); 73 μg pCMVR8.74 (gag, pol, tat, rev); and 625 μL 2M calcium ion solution. Total volume of solution B: 6.25 mL.

The solution B was thoroughly mixed, and while gently vortexing the solution A, the solution B was added dropwise, and allowed to stand for 5-15 minutes. The above mixed solution of A and B was gently vortexed, and added dropwise to a culture dish containing 293T cells. The culture dish was gently shaken back and forth to evenly distribute the mixture of DNA and calcium ions (the culture dish should not be rotated), and placed in an incubator and cultured for 16-18 hours. The medium was replaced with fresh medium and continued to culture. The lentivirus-containing supernatant was collected after 48 hours and 72 hours, respectively. The above culture fluid was centrifuged at 500 g for 10 min at 25° C., and filtered using a PES membrane (0.45

μm). A centrifuge tube (Blechman Coulter Ultra-clear SW28 centrifuge tube) was sterilized with 70% ethanol, and sterilized under a UV light for 30 min The filtered lentivirus-containing supernatant was transferred to a centrifuge tube. A layer of 20% sucrose was carefully spread on the bottom of the centrifuge tube (1 mL of sucrose was added per 8 mL of the supernatant). The centrifuge tube was equilibrated with PBS and centrifuged at 25,000 rpm (82,700 g) for 2 h at 4° C. The centrifuge tube was carefully taken out, the supernatant was discarded, and the centrifuge tube was inverted to remove residual liquid. The centrifuge tube was added with 100 μL of PBS, sealed, placed at 4° C. for 2 h with a gentle vortex every 20 minutes, and centrifuged at 500 g for 1 min (25° C.). The lentivirus-containing supernatant was collected, cooled on ice, and then stored at −80° C.

EXAMPLE 3

Preparation of PD-1 CAR-NK-92 Cells

The density of NK-92 cells was adjusted to $2-3\times10^5$/ml. The virus vector was added in a ratio of virus vector: cell Medium=1:5-10 (v/v), and 8 μg/ml of polybrene was also added. After 4 h, an equal amount of fresh complete medium (see ATCC instructions for complete medium formulation) was added to adjust the cell density to $1\times10^5$/ml to continue to culture. The next day, all the cells were centrifuged, and fresh medium was added to continue to culture. Fluid supplementation was performed every 1-2 days to maintain a cell density of $2-3\times10^5$/ml. After 72 h, PD1 antibody staining was performed, and at the same time, PD1-CAR NK-92 positive cells were obtained by flow sorting and were expanded. The color change, cell density, and cell morphology of the medium were observed daily and recorded accordingly.

FIG. 2A-F: Flow cytometry detection results. In the FIG. A, the sample injected in the flow cytometry was a common NK92 cell, and the cells in the circled area were living cells which were used for the analysis of FIGS. B and C. In the FIG. D, the sample injected in the flow cytometry was a PD-1 CAR NK-92 cell, and the cells in the circled area were living cells which were used for the analysis of FIGS. E and F. FIGS. B/E: the cells analyzed by this figure were stained with anti-PD1 antibody, and the antibody was conjugated with a PE fluorescent molecule; the larger the value of the abscissa PE-H in the figure, the more the positive cells stained by the antibody detected by the cytometery, that is, the more cells expressing the PD-1 molecule. Since the untransfected NK92 cells were analyzed in FIG. B, the FIG. B was used as a control, and a gate was painted in the FIG. B, in which cells positive for PD-1 molecule staining were shown in the gate, and cells negative for PD-1 molecule detection were shown in the area to the left of the gate. The FIG. E showed the detection of PD-1 CAR NK92 cells after transfecting and screening, which showed that the cells were distributed in the gate, indicating that the PD-1 molecule was expressed on the surface of the cell, proving that PD-1 NK-92 cells were successfully prepared. The FIG. C showed the untransfected NK92, which was not stained with an antibody and used for control. The FIG. F showed the detection of PD-1 CAR NK-92 cells prepared by transfecting with an anti-CD3ζ antibody (for identifying whether the cells were T cells) and an anti-CD56 antibody (for identifying whether the cells were NK cells), wherein the above antibodies were conjugated with APC and FITC fluorescent molecules, respectively. The larger abscissa and ordinate values indicate the higher expression of CD56 and CD3ζ molecules. The FIG. C was used as a control, which was not stained with an antibody, and the position in which the cells were distributed was used as a control, that is, the lower left area was considered to be negative for expression of CD3ζ and CD56 molecules. The test in the FIG. F showed that PD-1 CAR NK92 cells had no expression of CD3ζ molecule compared with control cells and were negative after staining; while after staining with CD56 antibody, PD-1 CAR NK92 cells had increased FTIC value, and were positive for the expression of CD56 molecule, which proved that the NK-92 cells obtained by screening did not change, and were still NK cells.

EXAMPLE 4

In Vitro Activity Assay of PD-1 CAR-NK Cells

Detection by CCK-8 method, i.e., the killing effect of PD-1 CAR-T and PD-1 CAR NK-92 cells on H1299 lung cancer cells were detected.

(1) 1 ml of H1299 cell suspension ($2\times10^4$ cells/well) was prepared in a 24-well plate. The plate was preincubated for 12 h in an incubator.

(2) The culture supernatant of the 24-well plate was discarded. 1 ml of effector cells were added to each well, and the ratio of the number of effector cells to the number of target cells was 1:1. Only 1 ml of medium was added to the control wells. Three replicate wells were set for each experiment. The effector cells were co-incubated with the target cells for 4 hours.

(3) 100 μl of CCK-8 solution was added to each well, and the plate was incubated for 2 h in an incubator.

(4) The absorbance at 450 nm was measured with a microplate reader.

(5) Specific lysis=(As−Ab)/(Ac−Ab)×100%

As: test well (medium containing H1299 cells, CCK-8, CAR-T or CAR-NK)

Ac: control well (medium containing H1299 cells, CCK-8)

Ab: blank control (cell- and CAR-T- or CAR-NK-free medium, CCK-8)

Figure 3:
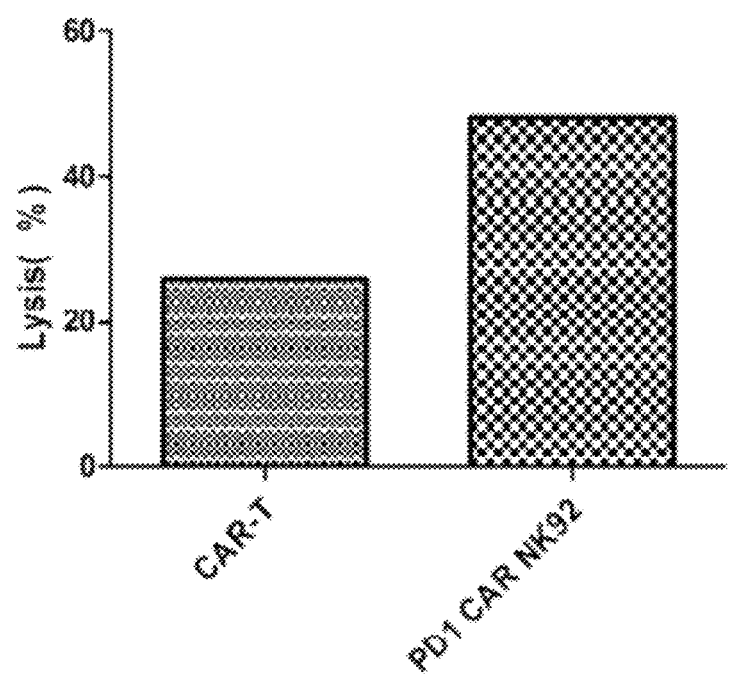
FIG. 3 is a graph showing the killing effect of PD-1 CAR-T and PD-1 CAR NK-92 cells on H1299 lung cancer cells detected by CCK-8 method.

As shown in the experimental results showed in FIG. 3, the prepared PD-1 CAR NK-92 cells were able to significantly kill the H1299 target cell line with high expression of PDL1, and had better killing effect than that of PD-1 CAR-T cells.

The PD-1 CAR NK-92 of the present invention is obtained by infecting PD-1 CAR molecules into a NK92 cell line and screening to obtain a single cloned cell by flow cytometry, and culturing and expanding the CAR NK92 monoclonal cell strain with stable traits and high killing activity. The cells can be produced on a large scale and can be used in different patients without GVHR rejection. Compared with CAR-T cells, PD-1 CAR NK-92 cells do not need to isolate a patient's peripheral blood mononuclear cells (PBMC), and do not require specific activation of T cells and preparation of CAR-T cells (this process requires the patient to wait more than 10 days), do not require individual customization, and can be used for multiple patients, shortening the time, and PD-1 CAR-NK92 cells can be prepared in large quantities and used immediately by patients; on the other hand, the conventionally prepared CAR-T cells are obtained by virus infection of T cells isolated from patients, wherein the T cells are not the same monoclonal source, while the sorted CAR-NK92 cells are derived from the same single clone, which are uniform and stable in characters and activity, and facilitate large-scale production and quality control. Furthermore, compared with NK92 cells, the CAR- NK92 cells have a specific killing activity and significant therapeutic effect on tumors due to the introduction of the PD-1 CAR vector.

The above is only the preferred embodiment of the present invention, and is not intended to limit the present invention. Any modifications, equivalent substitutions, improvements, etc., made within the spirit and scope of the present invention are intended to be included within the scope of the present invention.

The invention claimed is:

1. A PD-1 CAR NK-92 cell with expression of a PD-1-CD8-4-1BB-CD3ζ fusion protein in a NK-92 cell, wherein the extracellular portion of the PD-1 protein in the PD-1-CD8-4-1BB-CD3ζ fusion protein has an amino acid sequence as shown in SEQ ID NO: 5.

2. The PD-1 CAR NK-92 cell of claim 1, wherein the CD8 in the PD-1-CD8-4-1BB-CD3ζ fusion protein has: an amino acid sequence as shown in SEQ ID NO: 1, or, an amino acid sequence derived from the amino acid sequence as shown in SEQ ID NO: 1 by substituting and/or deleting and/or adding one or several amino acid residues and having the same function;

and/or, the CD3ζ in the PD-1-CD8-4-1BB-CD3ζ fusion protein has: an amino acid sequence as shown in SEQ ID NO: 4, or, an amino acid sequence derived from the amino acid sequence as shown in SEQ ID NO: 4 by substituting and/or deleting and/or adding one or several amino acid residues and having the same function.

3. The PD-1 CAR NK-92 cell of claim 1, wherein the 4-1BB in the PD-1-CD8-4-1BB-CD3ζ fusion protein has: an amino acid sequence as shown in SEQ ID NO: 2, or, an amino acid sequence derived from the amino acid sequence as shown in SEQ ID NO: 2 by substituting and/or deleting and/or adding one or several amino acid residues and having the same function;

or, the 4-1BB in the PD-1-CD8-4-1BB-CD3ζ fusion protein is replaced by CD28, and the CD28 has a molecular sequence as shown in SEQ ID NO: 3, or, an amino acid sequence derived from the amino acid sequence as shown in SEQ ID NO: 3 by substituting and/or deleting and/or adding one or several amino acid residues and having the same function.

4. The PD-1 CAR NK-92 cell of claim 1, wherein the PD-1-CD8-4-1BB-CD3ζ fusion protein has: an amino acid sequence as shown in SEQ ID NO: 6;

or, an amino acid sequence derived from the amino acid sequence as shown in SEQ ID NO: 6 by substituting and/or deleting and/or adding one or several amino acid residues and having the same function.

5. A gene encoding a fusion protein PD-1-CD8-4-1BB-CD3ζ, wherein the PD-1 protein in the PD-1-CD8-4-1BB-CD3ζ fusion protein has an amino acid sequence as shown in SEQ ID NO: 5.

6. The gene of claim 5, wherein the CD8 in the PD-1-CD8-4-1BB-CD3ζ fusion protein has: an amino acid sequence as shown in SEQ ID NO: 1, or, an amino acid sequence derived from the amino acid sequence as shown in SEQ ID NO: 1 by substituting and/or deleting and/or adding one or several amino acid residues and having the same function;

and/or, the CD3ζ in the PD-1-CD8-4-1BB-CD3ζ fusion protein has: an amino acid sequence as shown in SEQ ID NO: 4, or, an amino acid sequence derived from the amino acid sequence as shown in SEQ ID NO: 4 by substituting and/or deleting and/or adding one or several amino acid residues and having the same function.

7. The gene of claim 5, wherein the 4-1BB in the PD-1-CD8-4-1BB-CD3ζ fusion protein has: an amino acid sequence as shown in SEQ ID NO: 2, or, an amino acid sequence derived from the amino acid sequence as shown in SEQ ID NO: 2 by substituting and/or deleting and/or adding one or several amino acid residues and having the same function;

or, the 4-1BB in the PD-1-CD8-4-1BB-CD3ζ fusion protein is replaced by CD28, and the CD28 has a molecular sequence as shown in SEQ ID NO: 3, or, an amino acid sequence derived from the amino acid sequence as shown in SEQ ID NO: 3 by substituting and/or deleting and/or adding one or several amino acid residues and having the same function.

8. The gene of claim 5, wherein the PD-1-CD8-4-1BB-CD3ζ fusion protein has: an amino acid sequence as shown in SEQ ID NO: 6;

or, an amino acid sequence derived from the amino acid sequence as shown in SEQ ID NO: 6 by substituting and/or deleting and/or adding one or several amino acid residues and having the same function.

9. The gene of claim 5, wherein the fusion protein having a sequence as shown in SEQ ID NO: 7;

or, a DNA molecule hybridizing with the sequence as shown in SEQ ID NO: 7 under stringent conditions and encoding a related protein having a function of preventing and/or treating a tumor;

or, a DNA molecule having at least 90% or more, or 95% or more, or 98% or more homology to the sequence as shown in SEQ ID NO: 7 and encoding a related protein having a function of preventing and/or treating a tumor.

10. A pharmaceutical composition comprising the PD-1 CAR NK-92 cell of claim 1, and a pharmaceutically acceptable auxiliary material.

11. The pharmaceutical composition of claim 10, wherein the extracellular portion of the PD-1 protein in the PD-1-CD8-4-1BB-CD3ζ fusion protein has an amino acid sequence as shown in SEQ ID NO: 5;
and/or, the CD8 in the PD-1-CD8-4-1BB-CD3ζ fusion protein has: an amino acid sequence as shown in SEQ ID NO: 1, or, an amino acid sequence derived from the amino acid sequence as shown in SEQ ID NO: 1 by substituting and/or deleting and/or adding one or several amino acid residues and having the same function;
and/or, the CD3ζ in the PD-1-CD8-4-1BB-CD3ζ fusion protein has: an amino acid sequence as shown in SEQ ID NO: 4, or, an amino acid sequence derived from the amino acid sequence as shown in SEQ ID NO: 4 by substituting and/or deleting and/or adding one or several amino acid residues and having the same function.

12. The pharmaceutical composition of claim 10, wherein the 4-1BB in the PD-1-CD8-4-1BB-CD3ζ fusion protein has: an amino acid sequence as shown in SEQ ID NO: 2, or, an amino acid sequence derived from the amino acid sequence as shown in SEQ ID NO: 2 by substituting and/or deleting and/or adding one or several amino acid residues and having the same function;

or, the 4-1BB in the PD-1-CD8-4-1BB-CD3ζ fusion protein is replaced by CD28, and the CD28 has a molecular sequence as shown in SEQ ID NO: 3, or, an amino acid sequence derived from the amino acid sequence as shown in SEQ ID NO: 3 by substituting and/or deleting and/or adding one or several amino acid residues and having the same function.

13. The pharmaceutical composition of claim 10, wherein the PD-1-CD8-4-1BB-CD3ζ fusion protein has: an amino acid sequence as shown in SEQ ID NO: 6;

or, an amino acid sequence derived from the amino acid sequence as shown in SEQ ID NO: 6 by substituting and/or deleting and/or adding one or several amino acid residues and having the same function.

14. The pharmaceutical composition of claim 10, wherein the pharmaceutical composition is an injection.

15. A method for preventing and/or treating a tumor, including using the PD-1 CAR NK-92 cell of claim 1.

16. The method of claim 15, wherein the tumor is a tumor highly expressing PDL-1 molecule.

17. The method of claim 15, wherein the extracellular portion of the PD-1 protein in the PD-1-CD8-4-1BB-CD3ζ fusion protein has an amino acid sequence as shown in SEQ ID NO: 5;
and/or, the CD8 in the PD-1-CD8-4-1BB-CD3ζ fusion protein has: an amino acid sequence as shown in SEQ ID NO: 1, or, an amino acid sequence derived from the amino acid sequence as shown in SEQ ID NO: 1 by substituting and/or deleting and/or adding one or several amino acid residues and having the same function;
and/or, the CD3ζ in the PD-1-CD8-4-1BB-CD3ζ fusion protein has: an amino acid sequence as shown in SEQ ID NO: 4, or, an amino acid sequence derived from the amino acid sequence as shown in SEQ ID NO: 4 by substituting and/or deleting and/or adding one or several amino acid residues and having the same function.

18. The method of claim 15, wherein the 4-1BB in the PD-1-CD8-4-1BB-CD3ζ fusion protein has: an amino acid sequence as shown in SEQ ID NO: 2, or, an amino acid sequence derived from the amino acid sequence as shown in SEQ ID NO: 2 by substituting and/or deleting and/or adding one or several amino acid residues and having the same function;

or, the 4-1BB in the PD-1-CD8-4-1BB-CD3ζ fusion protein is replaced by CD28, and the CD28 has a molecular sequence as shown in SEQ ID NO: 3, or, an amino acid sequence derived from the amino acid sequence as shown in SEQ ID NO: 3 by substituting and/or deleting and/or adding one or several amino acid residues and having the same function.

19. The method of claim 15, wherein the PD-1-CD8-4-1BB-CD3ζ fusion protein has: an amino acid sequence as shown in SEQ ID NO: 6;

or, an amino acid sequence derived from the amino acid sequence as shown in SEQ ID NO: 6 by substituting and/or deleting and/or adding one or several amino acid residues and having the same function.

* * * * *

SEQUENCE LISTING

```
<160> NUMBER OF SEQ ID NOS: 12

<210> SEQ ID NO 1
<211> LENGTH: 24
<212> TYPE: PRT
<213> ORGANISM: Artificial Sequence
<220> FEATURE:
<223> OTHER INFORMATION: CD8TM

<400> SEQUENCE: 1

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 2
<211> LENGTH: 42
<212> TYPE: PRT
<213> ORGANISM: Artificial Sequence
<220> FEATURE:
<223> OTHER INFORMATION: 4-1BB

<400> SEQUENCE: 2

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 3
<211> LENGTH: 41
<212> TYPE: PRT
<213> ORGANISM: Artificial Sequence
<220> FEATURE:
<223> OTHER INFORMATION: CD28

<400> SEQUENCE: 3

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 4
<211> LENGTH: 112
<212> TYPE: PRT
<213> ORGANISM: Artificial Sequence
<220> FEATURE:
<223> OTHER INFORMATION: CD3??

<400> SEQUENCE: 4

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30
```

Asp Val Leu Asp Lys Arg Arg Gly Arg Asp Pro Glu Met Gly Gly Lys
                35                  40                  45

Pro Arg Arg Lys Asn Pro Gln Glu Gly Leu Tyr Asn Glu Leu Gln Lys
 50                  55                  60

Asp Lys Met Ala Glu Ala Tyr Ser Glu Ile Gly Met Lys Gly Glu Arg
 65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 5
<211> LENGTH: 170
<212> TYPE: PRT
<213> ORGANISM: Artificial Sequence
<220> FEATURE:
<223> OTHER INFORMATION: Extracellular portion of PD-1 protein

<400> SEQUENCE: 5

Met Gln Ile Pro Gln Ala Pro Trp Pro Val Val Trp Ala Val Leu Gln
 1               5                  10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
                35                  40                  45

Asn Ala Thr Phe Thr Cys Ser Phe Ser Asn Thr Ser Glu Ser Phe Val
 50                  55                  60

Leu Asn Trp Tyr Arg Met Ser Pro Ser Asn Gln Thr Asp Lys Leu Ala
 65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
        130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val
                165                 170

<210> SEQ ID NO 6
<211> LENGTH: 348
<212> TYPE: PRT
<213> ORGANISM: Artificial Sequence
<220> FEATURE:
<223> OTHER INFORMATION: PD-1-CD8TM-4-1BB-CD3?? fusion protein

<400> SEQUENCE: 6

Met Gln Ile Pro Gln Ala Pro Trp Pro Val Val Trp Ala Val Leu Gln
 1               5                  10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
                35                  40                  45

Asn Ala Thr Phe Thr Cys Ser Phe Ser Asn Thr Ser Glu Ser Phe Val
 50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Ile Tyr Ile Trp Ala Pro
                165                 170                 175

Leu Ala Gly Thr Cys Gly Val Leu Leu Leu Ser Leu Val Ile Thr Leu
            180                 185                 190

Tyr Cys Lys Arg Gly Arg Lys Lys Leu Leu Tyr Ile Phe Lys Gln Pro
        195                 200                 205

Phe Met Arg Pro Val Gln Thr Thr Gln Glu Glu Asp Gly Cys Ser Cys
    210                 215                 220

Arg Phe Pro Glu Glu Glu Glu Gly Gly Cys Glu Leu Arg Val Lys Phe
225                 230                 235                 240

Ser Arg Ser Ala Asp Ala Pro Ala Tyr Lys Gln Gly Gln Asn Gln Leu
                245                 250                 255

Tyr Asn Glu Leu Asn Leu Gly Arg Arg Glu Glu Tyr Asp Val Leu Asp
            260                 265                 270

Lys Arg Arg Gly Arg Asp Pro Glu Met Gly Gly Lys Pro Arg Arg Lys
        275                 280                 285

Asn Pro Gln Glu Gly Leu Tyr Asn Glu Leu Gln Lys Asp Lys Met Ala
    290                 295                 300

Glu Ala Tyr Ser Glu Ile Gly Met Lys Gly Glu Arg Arg Arg Gly Lys
305                 310                 315                 320

Gly His Asp Gly Leu Tyr Gln Gly Leu Ser Thr Ala Thr Lys Asp Thr
                325                 330                 335

Tyr Asp Ala Leu His Met Gln Ala Leu Pro Pro Arg
            340                 345

<210> SEQ ID NO 7
<211> LENGTH: 1194
<212> TYPE: DNA
<213> ORGANISM: Artificial Sequence
<220> FEATURE:
<223> OTHER INFORMATION: Nucleic acid encoding fusion protein
      PD-1-CD8TM-4-1BB-CD3??

<400> SEQUENCE: 7
atgcagatcc cacaggcgcc ctggccagtc gtctgggcgg tgctacaact gggctggcgg      60
ccaggatggt tcttagactc cccagacagg ccctggaacc ccccaccttt ctccccagcc    120
ctgctcgtgg tgaccgaagg ggacaacgcc accttcacct gcagcttctc caacacatcg    180
gagagcttcg tgctaaactg gtaccgcatg agccccagca accagacgga caagctggcc    240
gccttccccg aggaccgcag ccagcccggc caggactgcc gcttccgtgt cacacaactg    300
cccaacgggc gtgacttcca catgagcgtg gtcaggccc ggcgcaatga cagcggcacc    360
tacctctgtg gggccatctc cctggccccc aaggcgcaga tcaagagag cctgcgggca    420

| | |
|---|---|
| gagctcaggg tgacagagag aagggcagaa gtgcccacag cccacccag ccctcaccc | 480 |
| aggccagccg gccagttcca aaccctggtg accacgacgc cagcgccgcg accaccaaca | 540 |
| ccggcgccca ccatcgcgtc gcagcccctg tccctgcgcc cagaggcgtg ccggccagcg | 600 |
| gcgggggggca cagtgcacac gaggggggctg gacttcgcct gtgatatcta catctgggcg | 660 |
| cccttggccg ggacttgtgg ggtccttctc ctgtcactgg ttatcaccct ttactgcaac | 720 |
| cacaggaaca aacggggcag aaagaaactc ctgtatatat tcaaacaacc atttatgaga | 780 |
| ccagtacaaa ctactcaaga ggaagatggc tgtagctgcc gatttccaga agaagaagaa | 840 |
| ggaggatgtg aactgagagt gaagttcagc aggagcgcag acgccccgc gtaccagcag | 900 |
| ggccagaacc agctctataa cgagctcaat ctaggacgaa gagaggagta cgatgttttg | 960 |
| gacaagagac gtggccggga ccctgagatg ggggaaagc cgagaaggaa gaaccctcag | 1020 |
| gaaggcctgt acaatgaact gcagaaagat aagatggcgg aggcctacag tgagattggg | 1080 |
| atgaaaggcg agcgccggag gggcaagggg cacgatggcc tttaccaggg tctcagtaca | 1140 |
| gccaccaagg acacctacga cgcccttcac atgcaggccc tgccccctcg ctaa | 1194 |

```
<210> SEQ ID NO 8
<211> LENGTH: 510
<212> TYPE: DNA
<213> ORGANISM: Artificial Sequence
<220> FEATURE:
<223> OTHER INFORMATION: Nucleic acid encoding PD-1

<400> SEQUENCE: 8
```

| | |
|---|---|
| atgcagatcc cacaggcgcc ctggccagtc gtctgggcgg tgctacaact gggctggcgg | 60 |
| ccaggatggt tcttagactc cccagacagg ccctggaacc cccccacctt ctccccagcc | 120 |
| ctgctcgtgg tgaccgaagg ggacaacgcc accttcacct gcagcttctc caacacatcg | 180 |
| gagagcttcg tgctaaactg gtaccgcatg agccccagca accagacgga caagctggcc | 240 |
| gccttccccg aggaccgcag ccagcccggc caggactgcc gcttccgtgt cacacaactg | 300 |
| cccaacgggc gtgacttcca catgagcgtg gtcaggggcc ggcgcaatga cagcggcacc | 360 |
| tacctctgtg ggccatctc cctggcccc aaggcgcaga tcaaagagag cctgcgggca | 420 |
| gagctcaggg tgacagagag aagggcagaa gtgcccacag cccacccag ccctcaccc | 480 |
| aggccagccg gccagttcca aaccctggtg | 510 |

```
<210> SEQ ID NO 9
<211> LENGTH: 135
<212> TYPE: DNA
<213> ORGANISM: Artificial Sequence
<220> FEATURE:
<223> OTHER INFORMATION: Nucleic acid encoding CD 8 Hinge

<400> SEQUENCE: 9
```

| | |
|---|---|
| accacgacgc cagcgccgcg accaccaaca ccggcgccca ccatcgcgtc gcagcccctg | 60 |
| tccctgcgcc cagaggcgtg ccggccagcg gcgggggggcg cagtgcacac gaggggggctg | 120 |
| gacttcgcct gtgat | 135 |

```
<210> SEQ ID NO 10
<211> LENGTH: 84
<212> TYPE: DNA
<213> ORGANISM: Artificial Sequence
<220> FEATURE:
<223> OTHER INFORMATION: Nucleic acid encoding CD8TM
```

```
<400> SEQUENCE: 10
atctacatct gggcgccctt ggccgggact tgtggggtcc ttctcctgtc actggttatc    60 acccttact gcaaccacag gaac                                            84

<210> SEQ ID NO 11
<211> LENGTH: 126
<212> TYPE: DNA
<213> ORGANISM: Artificial Sequence
<220> FEATURE:
<223> OTHER INFORMATION: Nucleic acid encoding 4-1BB

<400> SEQUENCE: 11
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                              126

<210> SEQ ID NO 12
<211> LENGTH: 339
<212> TYPE: DNA
<213> ORGANISM: Artificial Sequence
<220> FEATURE:
<223> OTHER INFORMATION: Nucleic acid encoding CD3??

<400> SEQUENCE: 12
agagtgaagt tcagcaggag cgcagacgcc cccgcgtacc agcagggcca gaaccagctc    60
tataacgagc tcaatctagg acgaagagag gagtacgatg ttttggacaa gagacgtggc   120
cgggaccctg agatgggggg aaagccgaga aggaagaacc ctcaggaagg cctgtacaat   180
gaactgcaga agataagat ggcggaggcc tacagtgaga ttgggatgaa aggcgagcgc   240
cggaggggca aggggcacga tggcctttac cagggtctca gtacagccac caaggacacc   300
tacgacgccc ttcacatgca ggccctgccc cctcgctaa                          339
```